United States Patent [19]

Takekawa

[11] 4,452,759

[45] Jun. 5, 1984

[54] IMMUNOLOGICAL AGGLUTINATION PATTERN DETECTION DEVICE

[75] Inventor: Hiroshi Takekawa, Kunitachi, Japan

[73] Assignee: Olympus Optical Company Limited, Japan

[21] Appl. No.: 184,319

[22] Filed: Sep. 5, 1980

[30] Foreign Application Priority Data

Sep. 10, 1979 [JP] Japan .................... 54-123909

[51] Int. Cl.$^3$ ............................ G01N 33/54
[52] U.S. Cl. ........................ 422/73; 356/39; 356/442; 422/102; 436/805
[58] Field of Search .............. 356/39, 340, 246, 427, 356/434, 436, 440, 442, 444; 23/230 B; 422/73, 72, 102, ; 435/808, 291; 436/805

[56] References Cited

U.S. PATENT DOCUMENTS

| | | | |
|---|---|---|---|
| 2,788,702 | 4/1957 | Baum, Jr. | 356/340 |
| 3,520,609 | 7/1970 | Lion | 356/39 |
| 3,579,306 | 5/1971 | Crane | 422/61 |
| 3,883,308 | 5/1978 | Matte | 23/259 |
| 4,148,607 | 4/1979 | Bernoco et al. | 422/72 X |
| 4,150,360 | 4/1979 | Kopp et al. | 356/39 X |
| 4,232,970 | 11/1980 | Sawamura et al. | 356/39 X |
| 4,240,751 | 12/1980 | Linnecke et al. | 435/808 X |
| 4,303,616 | 12/1981 | Kano et al. | 422/73 X |

FOREIGN PATENT DOCUMENTS 1539674 10/1968 France .

OTHER PUBLICATIONS

Blume et al., *Clin. Chem.* 21/9, 1234–1237 (1975).
Stull, *Clin. Chem.* 19/8, 883–890 (1973).
Kaye et al., *J. Phys. E: Sci. Instrum.*, vol. 12, No. 8, Aug. 1979.

Primary Examiner—Arnold Turk
Attorney, Agent, or Firm—Parkhurst & Oliff

[57] ABSTRACT

An immunological agglutination pattern detection device, which can precisely detect an agglutination pattern formed on the base surface of a reaction vessel and which is simple in construction and easy in operation. The device comprises a reaction vessel provided with a base surface which is provided with at least one concave portion and a centrally located V-shaped section, a point light source for emitting light for evenly illuminating the base surface of the reaction vessel, a projection lens for projecting an image formed on the base surface of the reaction vessel illuminated with the light emitted from the point light source onto an image formation surface, apparatus for scanning the image formed on the image surface inclusive of the image of the agglutination pattern, and a light receiving element for receiving the image scanned by the scanning means and delivering an output signal.

4 Claims, 14 Drawing Figures

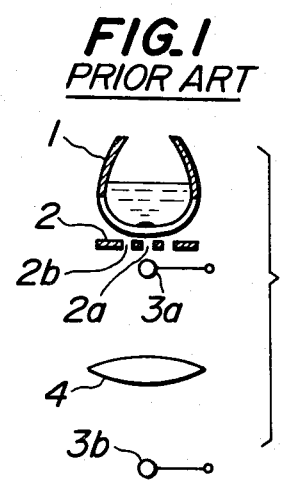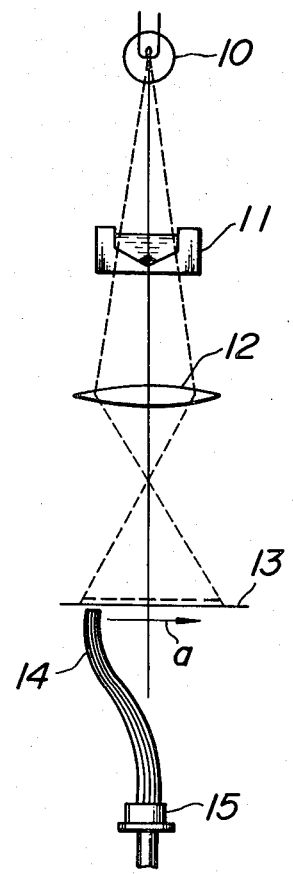

IMMUNOLOGICAL AGGLUTINATION PATTERN DETECTION DEVICE

BACKGROUND OF THE INVENTION

1. Field of the Invention

This invention relates to an immunological agglutination pattern detection device and more particularly to a blood corpuscle agglutination pattern detection device for determining various kinds of types of blood and detecting an antic body and antigen from agglutination patterns of the blood corpuscles.

2. Description of the Prior Art

Such kind of agglutination pattern detection device has been well known. In a conventional agglutination pattern detection device, use is made of a wine cup-shaped reaction vessel into which are quantitatively injected a floating liquid obtained by centrifuge and containing 2 to 5% of test blood corpuscles and a given antiserum. These floating liquid and antiserum are agitated, kept stationary and then subjected to centrifugal precipitation. Then, the reaction vessel is intensely shaken so as to separate the blood corpuscles from each other and then subjected to relatively slow oscillations to agglutinate the blood corpuscles into a center part of the base surface of the reaction vessel, thereby forming an agglutination pattern. Lights transmitted through the center portion and peripheral portion of the pattern are incident through a center opening and concentric peripheral opening of a diaphragm on first and second light receiving elements, respectively. In this case, the light passing through the peripheral opening is incident through a condenser lens on the second light receiving element.

In such conventional agglutination pattern detection device, if the blood corpuscles are not agglutinated, the amount of light passing through the center portion of the reaction vessel becomes small, whereas the amount of light passing through the peripheral portion of the reaction vessel becomes large. On the contrary, if the blood corpuscles are agglutinated, the light passing through the center portion of the reaction vessel becomes substantially equal to the light passing through the peripheral portion of the reaction vessel, the amount of light being intermediate between the small amount of light passing through the center portion of the reaction vessel and the large amount of light passing through the peripheral portion of the reaction vessel. As a result, it is possible to determine whether or not the blood corpuscles are agglutinated by means of the output signals delivered from the first and second light receiving elements.

The use of the above mentioned conventional agglutination pattern detection device has a number of disadvantages. In the first place, use must be made of two light receiving elements and hence the detection device is complex in construction. Secondly, the output level of these two light receiving elements are required to be adjusted beforehand by means of a reference agglutination pattern, so that the detection device is troublesome in operation. Third, the reference agglutination pattern involved to adjust the output level of the two light receiving elements is not always coincident with the agglutination pattern of a test body used in practice, so that the determination becomes erroneous. Finally, the conventional device for forming the agglutination pattern is required to cause non-agglutination blood corpuscles to float again on the test liquid, and as a result, it is necessary to shake the reaction vessel, thereby making the device troublesome in operation. In addition, if the reaction vessel is shaken, the blood corpuscles, which have once been agglutinated becomes separated. As a result, the above mentioned device is only applicable to the strong agglutination, but could not be applied to the weak agglutination.

In order to determine the presence or absence of the immunological agglutination and measure the degree of such agglutination with regard to the weak agglutination, a device for detecting the agglutination pattern formed on a conical base surface of a reaction vessel by making it stationary has also been proposed. In such conventional device, the agglutination pattern formed on the base surface of the reaction vessel is not always clear and accurate and hence it is impossible to precisely detect the agglutination pattern.

SUMMARY OF THE INVENTION

An object of the invention, therefore, is to provide an immunological agglutination pattern detection device which can eliminate the above mentioned drawbacks which have been encountered with the prior art techniques, which can precisely detect agglutination pattern formed on the base surface of a reaction vessel and which is simple in construction and easy in operation.

A feature of the invention is the provision of an immunological agglutination pattern detection device comprising a reaction vessel provided with a base surface which is provided with at least one concave portion and a centrally located V-shaped section for collecting particles contained in the vessel to create an agglutination pattern that is indicative of the amount of particles contained in the vessel, a point light source for emitting light for evenly illuminating the base surface of the reaction vessel, a projection lens for projecting an image formed on the base surface of the reaction vessel illuminated with the light emitted from the point light source onto an image formation surface, means for scanning the image formed on said image formation surface inclusive of the image of the agglutination pattern, and a light receiving element for receiving the image scanned by said scanning means and delivering an output signal.

Further objects and features of the invention will be fully understood from the following detailed description with reference to the accompanying drawings, wherein:

BRIEF DESCRIPTION OF THE DRAWINGS

FIG. 1 is a diagrammatic view of a conventional agglutination pattern detection device;

FIG. 2 is a diagrammatic view of one embodiment of an immunological agglutination pattern detection device according to the invention;

DETAILED DESCRIPTION OF THE PREFERRED EMBODIMENTS

Figure 3A:
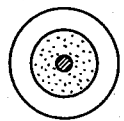
FIG. 3A is a plan view of a collect pattern formed by non-agglutination.

FIG. 1 shows a conventional agglutination pattern detection device which makes use of a wine cup-shaped reaction vessel 1. Into the reaction vessel 1 are quantitatively injected a floating liquid obtained by centrifuge and containing 2 to 5% of test blood corpuscles and a given antiserum are agitated, kept stationary and then subjected to centrifugal precipitation. Then, the reaction vessel is intensely shaken so as to separate the precipitated blood corpuscles from each other and then subjected to relatively slow oscillations to collect the agglutinated ingredients into the centrally located V-shaped portion of the reaction vessel 1, thereby forming an agglutination pattern. Light transmitted through the centrally located V-shaped portion and peripheral portion of the agglutination pattern is incident through a diaphragm 2 provided at its centrally located V-shaped portion with an opening 2a and at its periphery with a concentric opening 2b onto light receiving elements 3a and 3b, respectively. In this case, the light passed through the peripheral opening 2b is incident through a condenser lens 4 onto the second light receiving element 3b. In such conventional agglutination pattern detection device, if blood corpuscles, for example, are agglutinated, the amount of light passing through the centrally located U-shaped portion becomes small, whereas the amount of light passing through the peripheral portion becomes large. On the contrary, if the blood corpuscles are not agglutinated, the amount of light transmitted through the centrally located V-shaped portion becomes substantially equal to the amount of light transmitted through the peripheral portion, the amount of light being intermediate between the amount of light transmitted through the centrally located V-shaped portion and the amount of light transmitted through the peripheral portion when the blood corpuscles are agglutinated. As a result, it is possible to determine by the output delivered from the light receiving elements 3a and 3b whether or not the blood corpuscles are agglutinated.

Such kind of conventional agglutination pattern detection device has a number of disadvantages. In the first place, use must be made of two light receiving elements 3a and 3b, thereby making the detection device complex in construction. Secondly, it is required to adjust beforehand the output level of the two light receiving elements 3a and 3b by means of a reference agglutination pattern, and as a result, the device is troublesome in operation. Third, the reference agglutination pattern involved to adjust the output level of the two light receiving elements 3a and 3b is not always coincident with the agglutination pattern of a test body used in practice, so that there is a risk of the determination being subjected to error. Fourth, a conventional agglutination pattern formation device is required to cause non-agglutinated blood corpuscles to float again on the test liquid and hence is required to perform shaking operation, and as a result, the detection device is troublesome in operation. Finally, the shaking operation results in separation of the blood corpuscles which have once been agglutinated, so that the detection device is only applicable to strong agglutination, but could not be applied to weak agglutination.

In order to measure presence, absence or degree of an immunological agglutination whose agglutinative force is weak, a device for detecting an agglutination pattern formed on a conical base surface of a reaction vessel by keeping stationary has heretofore been proposed. Such conventional detection device has the disadvantage that the agglutination pattern formed on the base surface of the reaction vessel is not always clear and accurate. As a result, such conventional detection device could not precisely detect whether or not agglutination pattern occurs.

FIG. 2 shows one embodiment of an agglutination pattern detection device according to the invention. In the present embodiment, provision is made of a point light source 10 which functions to evenly illuminate a base surface which is provided with at least one concave portion of a reaction vessel 11. In the present embodiment, the base surface of the reaction vessel 11 is provided at its center with a concave portion. In the case of determining blood types A, B and O, for example, the blood extracted from a test body is centrifugally separated into blood corpuscles and serum and then a floating liquid containing the blood corpuscles is prepared. The floating liquid is then quantitatively injected into the reaction vessel 11. Subsequently, a given amount of antiserum having a given type of antibody is injected into the reaction vessel 11 and the whole is agitated and then kept stationary. In this case, if the test blood is A type and the antiserum contains A type of antibody, then there occurs no agglutination. As a result, blood corpuscles are not agglutinated and are settled down in separated state. When these blood corpuscles reach the concave portion of the base surface of the reaction vessel 11, these particles are tumbled down along the inclined surface onto the bottom portion of the concave portion of the base surface to form a collected pattern as shown in FIG. 3A.

Figure 3B:
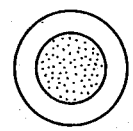
FIG. 3B is a plan view of an evenly deposited pattern formed by agglutination.

If the test blood is B type, there occurs agglutination and the blood corpuscles are settled down like snowflakes and evenly deposited on the base surface of the reaction vessel 11 to form an even and thin deposit pattern as shown in FIG. 3B.

Figure 3C:
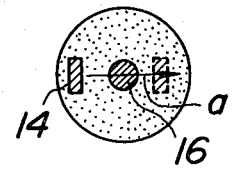
FIG. 3C is a plan view showing a relation between a projected image of the collection pattern and an incident end of a scanning element.
Figure 3D:
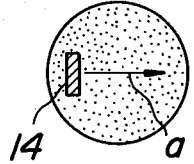
FIG. 3D is a plan view showing a relation between a projected image of the even deposit pattern and an incident end of a scanning element.

The present invention has its object of precisely detecting the above mentioned evenly deposited agglutination pattern. In the present invention, in order to attain such object, the image formed on the base surface of the reaction vessel 1 is focused onto a predetermined image formation surface 13 by means of a projection lens 12. In the present embodiment, provision is made of a flexible light guide 14 having a light incident end opposed to the image formation surface 13 and a light emitting end opposed to a light receiving element 15. The light incident end is made movable along the image formation surface 13 as shown by an arrow a in FIG. 2 by means of a suitable driving mechanism. As a result, it is possible to scan the image of a base surface of the reaction vessel 11 in a diametrical direction as shown in FIGS. 3C and 3D by means of the light incident end of the flexible light guide 14. The light incident end of the light guide 14 may be made rectangular, circular or the like in shape. It is preferable, however, to make the cross-sectional area of the light incident end of the light guide 14 substantially equal to or smaller than a center dark portion 16 of the collect pattern formed when no agglutination occurs as shown in FIG. 3C.

Figure 3E:
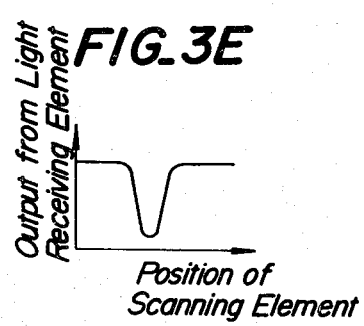
FIG. 3E is a graph illustrating an output delivered from a light receiving element as a function of a position of a scanning element for scanning a collect pattern.
Figure 3F:
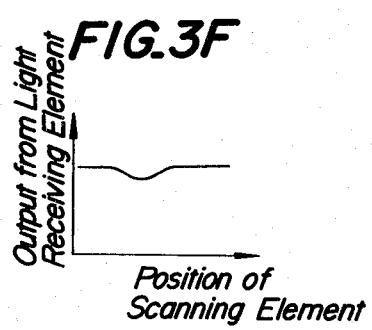
FIG. 3F is a graph illustrating an output delivered from a light receiving element as a function of a position of a scanning element for scanning an even deposit pattern.

In the case of scanning the image of the base surface of the reaction vessel 11 formed on the image formation surface 13 by the light guide 14, when no agglutination occurs an output signal is delivered from the light receiving element 15 as shown in FIG. 3E and when agglutination occurs an output signal is delivered from the light receiving element 15 as shown in FIG. 3F.

That is, when agglutination occurs, an evenly deposited agglutination patterns as shown in FIG. 3B is formed and the output delivered from the light receiving element 15 when the incident end of the light guide 14 scans the centrally located V-shaped portion of the base surface of the reaction vessel 11 is substantially the same as the output delivered from the light receiving element 15 when the incident end of the light guide 14 scans the peripheral portion of the base surface of the reaction vessel 11.

On the contrary, when no agglutination occurs, a collect pattern as shown in FIG. 3A is formed and the output delivered from the light receiving element 15 when the incident end of the light guide 14 scans the centrally located V-shaped portion of the base surface of the reaction vessel 11 is considerably different from the output delivered from the light receiving element 15 when the incident end of the light guide 14 scans that image of the peripheral portion of base surface of the reaction vessel 11 which is formed on the image formation surface 13 as shown in FIG. 3E.

As a result, it is possible to detect presence and absence or degree of agglutination or the like by examining the wave form of the output delivered from the light receiving element 15.

Figure 4:
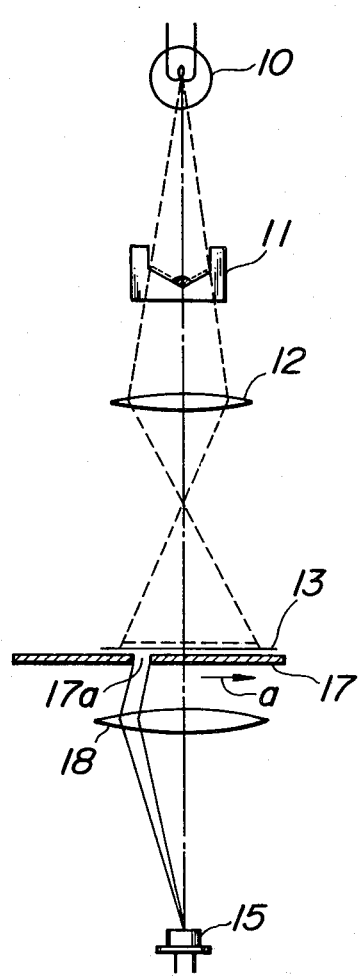
FIG. 4 is a diagrammatic view of another embodiment of an immunological agglutination pattern detection device according to the invention.

FIG. 4 shows another embodiment of a detection device according to the present invention. In the present embodiment, use is made of a slit plate 17 in place of the light guide 14 shown in FIG. 2. The slit plate 17 is provided with a slit opening 17a and movably arranged along the image formation surface 13. In the present embodiment, light passed through the slit opening 11a is incident through a lens 18 on the light receiving element 15.

If the slit plate 17 is moved in a direction shown by an arrow a, it is possible to scan the image of the base surface of the reaction vessel 11 formed on the image formation surface 13 and cause the light receiving element 15 to deliver an output in the same manner as described with reference to FIG. 3. In this case, the shape of the opening 17a of the slit plate 17 may be made rectangular, circular or the like. The area of the opening 17a may be made substantially equal to or smaller than the area of the center dark portion 16 of the collected pattern formed when no agglutination occurs in the same manner as the area of the center dark portion 16 of the collected pattern formed when no agglutination occurs in the same manner as the area of the incident end of the light guide 14 described with reference to the previous embodiment shown in FIG. 2.

Figure 5:
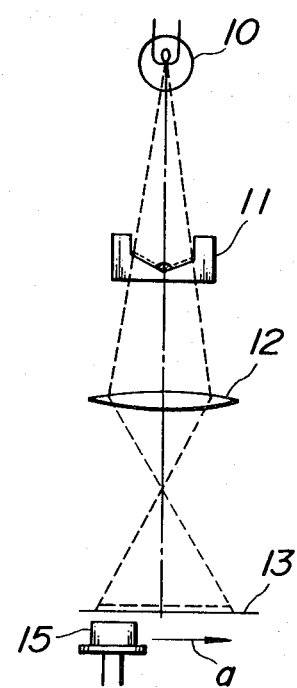
FIG. 5 is a diagrammatic view of a further embodiment of an immunological agglutination pattern detection device according to the invention.
Figure 6:
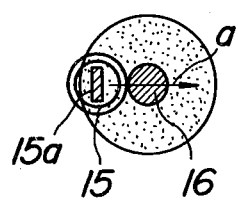
FIG. 6 is a plan view of a collect pattern formed on a light receiving surface by the detection device shown in FIG. 5.

FIG. 5 shows a further embodiment of a detection device according to the invention. In the present embodiment, the light receiving element 15 is movably arranged along the image formation surface 13 on which is formed through the lens 12 the image of the base surface of the reaction vessel 11 illuminated by the point light source 10. If the light receiving element 15 is moved in a direction shown by an arrow a, it is possible to scan the image of the base surface of the reaction vessel 11. The light receiving element 15 may be provided at its incident end with a slit 15a as shown in FIG. 6 for the purpose of attaining effective scanning. If the effective light receiving surface of the incident end of the light receiving element 15 is sufficiently small, such slit 15a may be omitted.

Figure 7:
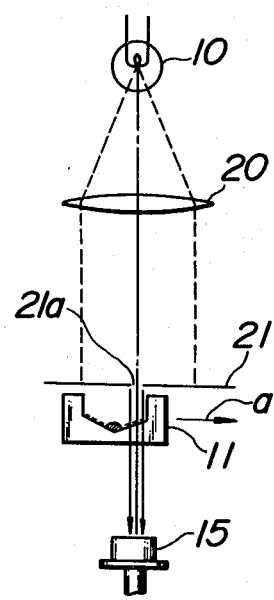
FIG. 7 is a diagrammatic view of a still further embodiment of an immunological agglutination pattern detection device according to the invention.

FIG. 7 shows a still further embodiment of a detection device according to the invention. In the present embodiment, the light emitted from the point light source 10 is made parallel light flux by means of a collimator lens 20 and then incident through a slit opening 21a of a slit plate 21 on the reaction vessel 11 to illuminate the base surface thereof. The light transmitted through the reaction vessel 11 is received by the light receiving element 15. The area of the slit opening 21a is made substantially equal to or smaller than the area of the center dark portion 16 of the collected pattern formed when no agglutination occurs in the same manner as the area of the incident end of the light guide 14 shown in FIG. 2.

In the present embodiment, if the reaction vessel 11 is moved in a direction shown by an arrow a relative to the light beam passed through the slit opening 21a, it is possible to scan the agglutination pattern formed on the base surface of the reaction vessel 11 and hence obtain the outputs shown in FIGS. 3E, 3F from the light receiving element 15.

Figure 8:
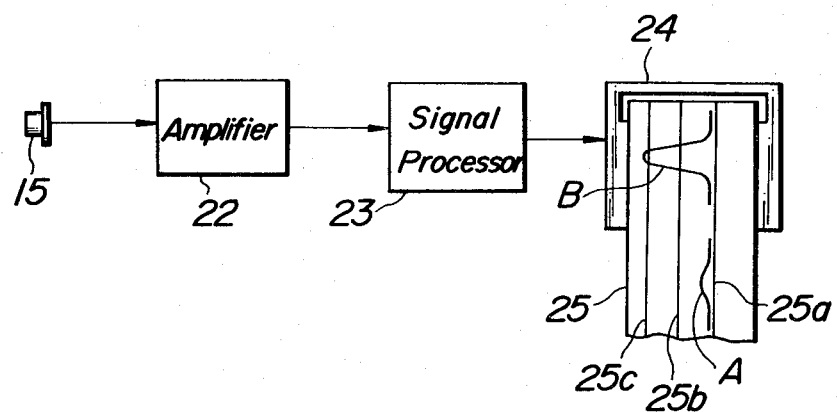
FIG. 8 is a circuit diagram of one example of a circuit for treating an output signal delivered from a light receiving element of a detection device according to the invention and determining agglutination or non-agglutination.

FIG. 8 shows an embodiment of a device for treating the output delivered from the light receiving element 15 so as to discriminate the agglutination pattern from the non-agglutination pattern. The output delivered from the light receiving element 15 is amplified by an amplifier 22 and then supplied to a signal processor 23 to adjust the level of the signal. The output delivered from the signal processor 27 is supplied to a recording meter 24 which functions to record the output on a recording sheet 25. On the recording sheet 25 are printed beforehand a base line 25a, an agglutination discrimination reference line 25b and non-agglutination discrimination reference line 25c. The signal processor 23 functions to bring an initial value of the output signal into alignment with the base line 25a.

If a curve A is plotted on the recording sheet 25 shown in FIG. 8, that is, if the peak of the curve A does not exceed the reference line 25b, it is possible to determine that there occurs an even deposited agglutination pattern. On the contrary, if a curve B is plotted on the recording sheet 25, that is, if the peak of curve B exceeds the reference lines 25b and 25c, it is possible to determine that there occurs a collected non-agglutination pattern. It is a matter of course that a condition intermediate between the above mentioned two conditions can be detected. For example, if the peak of the curve plotted on the recording sheet 25 exceeds one of the reference lines 25b, but does not exceed the other reference line 25c, it is possible to determine that a semi-collected pattern is formed and an intermediate agglutination occurs.

Figure 9:
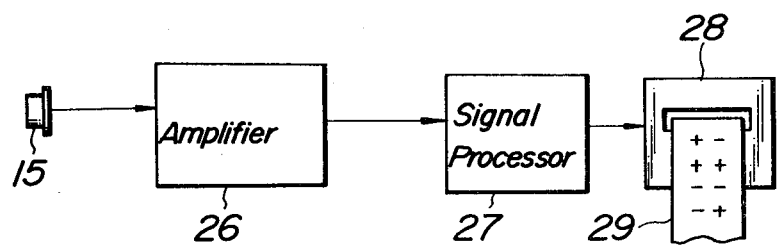
FIG. 9 is a circuit diagram of another example of a circuit for treating an output signal delivered from a light receiving element of a detection device according to the invention and determining agglutination or non-agglutination.

FIG. 9 shows another embodiment of a signal treating device according to the invention. In the present embodiment, the output delivered from the light receiving element 15 is amplified by an amplifier 26 and then supplied to a signal processor 27. The signal processor 27 functions to detect a difference between a maximum value of the signal and a minimum value of the signal and compare this difference with a preset reference value. If difference does not exceed the reference value, for example, + is printed on a record sheet 29 in a printer 28, whereas if the difference exceeds the reference value, − is printed on the record sheet 29. In this way, if agglutination occurs, + is printed on the record sheet 29, whereas if no agglutination occurs, − is printed on the record sheet 29. As a result, it is possible to determine whether or not agglutination occurs.

What is claimed is:

1. An immunological agglutination pattern detection device that includes
    a stationary reaction vessel having a concave interior base surface that includes a centrally located V-shaped section for collecting particles contained in the vessel to create an agglutination pattern that is indicative of the amount of particles contained in the vessel,
    a point light source positioned on one side of the base surface for uniformly illminating the base surface to create a light image of the agglutination pattern,
    an image forming surface positioned on the opposite side of the base surface for receiving the light image of said agglutination pattern,
    a projection lens for focusing a light image of the agglutination pattern upon the image forming surface,
    a slit plate mounted adjacent to said image forming surface which has a light aperture formed therein,
    means for moving the slit plate in relation to said image forming surface whereby the aperture of the slit scans the image focused upon said surface, and
    a light detecting means for receiving light passed through said aperture and providing an output signal indicative of the agglutination pattern.

2. The device of claim 1 that further includes a recording means for processing the output signal of said detecting means and providing a discernable record of the agglutination pattern.

3. The device of claim 1 wherein the base surface of the vessel is conical in form.

4. The device of claim 1 that further includes a second lens for bringing the scanned image to the detecting means.

* * * * *